(12) United States Patent
Motomura et al.

(10) Patent No.: US 12,305,155 B2
(45) Date of Patent: May 20, 2025

(54) QUALITY EVALUATION METHOD

(71) Applicants: Sumitomo Electric Industries, Ltd., Osaka (JP); Cyfuse Biomedical K.K., Tokyo (JP); National University Corporation Tokai National Higher Education and Research System, Nagoya (JP)

(72) Inventors: Asako Motomura, Osaka (JP); Yoko Sugiyama, Osaka (JP); Hiroshi Suganuma, Osaka (JP); Akinori Kimura, Osaka (JP); Shizuka Akieda, Tokyo (JP); Yudai Miyazaki, Tokyo (JP); Ryuji Kato, Nagoya (JP); Mayu Shibuta, Nagoya (JP); Ryohei Yamamoto, Nagoya (JP)

(73) Assignees: Sumitomo Electric Industries, Ltd., Osaka (JP); Cyfuse Biomedical K.K., Tokyo (JP); National University Corporation Tokai National Higher Education and Research System, Nagoya (JP)

( * ) Notice: Subject to any disclaimer, the term of this patent is extended or adjusted under 35 U.S.C. 154(b) by 484 days.

(21) Appl. No.: 17/338,841

(22) Filed: Jun. 4, 2021

(65) Prior Publication Data

US 2021/0293704 A1    Sep. 23, 2021

Related U.S. Application Data

(63) Continuation of application No. PCT/JP2019/048342, filed on Dec. 10, 2019.

(30) Foreign Application Priority Data

Dec. 13, 2018  (JP) ................... 2018-233525

(51) Int. Cl.
*C12M 1/00* (2006.01)
*G01N 21/59* (2006.01)
(Continued)

(52) U.S. Cl.
CPC ............ *C12M 31/02* (2013.01); *G01N 21/59* (2013.01); *G06V 10/36* (2022.01); *G06V 10/54* (2022.01);
(Continued)

(58) Field of Classification Search
None
See application file for complete search history.

(56) References Cited

U.S. PATENT DOCUMENTS 5,643,561 A  *  7/1997  Katsuen ............... C09D 189/04
                                                            435/395
9,469,833 B2 * 10/2016  Nakayama ............. C12M 33/00
(Continued)

FOREIGN PATENT DOCUMENTS

JP   2008-261631 A   10/2008
WO   2006/095896 A1  9/2006
(Continued)

OTHER PUBLICATIONS

Akieda et al., "Development of non-destructive and non-invasive quality evaluation method for spheroid (cell mass) and 3D tissue," Regenerative medicine, extra edition, Programs and abstracts of the 15th Congress of the Japanese Society for Regenerative Medicine, 2016, vol. 15, suppl., p. 350.

Nagai, et al., "Non-invasive quality evaluation of spheroids using near-infrared light imager," Lecture abstracts of the 71st SBJ Annual meeting, 2019, p. 183.

*Primary Examiner* — Mary Ellen Bowman
*Assistant Examiner* — Chad Andrew Reverman
(74) *Attorney, Agent, or Firm* — McCarter & English, LLP; Michael A. Sartori

(57) ABSTRACT

A method for quality evaluation includes emitting measurement light having a wavelength of 300 nm or more and 2,000
(Continued)

nm or less to a cell mass and acquiring a plurality of light intensity information corresponding to each of a plurality of measuring positions in the cell mass, generating a feature amount from a variation of the acquired plurality of light intensity information, and evaluating quality of the cell mass using the generated feature amount as an index.

5 Claims, 16 Drawing Sheets

(51) Int. Cl.
*G06V 10/36* (2022.01)
*G06V 10/54* (2022.01)
*G06V 10/98* (2022.01)
*G06V 20/69* (2022.01)

(52) U.S. Cl.
CPC .......... *G06V 10/993* (2022.01); *G06V 20/695* (2022.01); *G06V 20/698* (2022.01)

(56) References Cited

U.S. PATENT DOCUMENTS

| | | | |
|---|---|---|---|
| 11,092,542 B2 * | 8/2021 | Suganuma | C12M 41/36 |
| 2010/0260722 A1 * | 10/2010 | Ebisawa | C12N 5/0629 |
| | | | 424/93.7 |
| 2012/0142095 A1 * | 6/2012 | Yano | C12M 41/14 |
| | | | 435/325 |
| 2017/0254741 A1 * | 9/2017 | Suganuma | G01N 21/01 |
| 2017/0350805 A1 * | 12/2017 | Murata | G01N 21/27 |
| 2017/0358081 A1 | 12/2017 | Tsumura | |
| 2019/0137389 A1 * | 5/2019 | Suganuma | G01N 33/4833 |
| 2021/0293704 A1 * | 9/2021 | Motomura | G01N 15/1433 |

FOREIGN PATENT DOCUMENTS

| | | | | |
|---|---|---|---|---|
| WO | 2010/143420 A1 | 12/2010 | | |
| WO | 2015/145872 A1 | 10/2015 | | |
| WO | WO-2016080442 A1 * | 5/2016 | | G01J 3/42 |
| WO | 2018/008240 A1 | 11/2018 | | |

* cited by examiner

Fig.5

| a | b | c |
|---|---|---|
| d | e | f |
| g | h | i |

*Fig.7*

| 1 | 1 | 1 | 1 |
|---|---|---|---|
| 1 | 2 | 2 | 2 |
| 1 | 2 | 3 | 4 |
| 1 | 2 | 4 | 5 |

*Fig.8*

VALUE OF ADJACENT PIXEL

| | j=1 | j=2 | j=3 | j=4 | j=5 |
|---|---|---|---|---|---|
| i=1 | 2+3+2+ 1+3+2+ 1 | 1+2+3+ 2+2+3+ 2 | 0 | 0 | 0 |
| i=2 | 5+3+2+ 3+2 | 2+3+1+ 3+1 | 1+1+1+ 1+1 | 0+1+1+ 1+1 | 0 |
| i=3 | 0 | 5 | 0 | 2 | 1 |
| i=4 | 0 | 2+2 | 1+1 | 1+1 | 1+1 |
| i=5 | 0 | 0 | 1 | 2 | 0 |

VALUE OF CENTER PIXEL

QUALITY EVALUATION METHOD

TECHNICAL FIELD

The present disclosure relates to a quality evaluation method for cell masses. Priority is claimed on Japanese Patent Application No. 2018-233525, filed Dec. 13, 2018, the content of which is incorporated herein by reference.

BACKGROUND ART

Patent Literature 1 discloses a configuration in which time-series images of cell masses are acquired and evaluated in order to confirm a state of multi-layered cell masses.

CITATION LIST

Patent Literature

[Patent Literature 1] PCT International Publication No. WO 2010/143420

SUMMARY OF INVENTION

A quality evaluation method according to one aspect of the present disclosure includes emitting measurement light having a wavelength of 300 nm or more and 2,000 nm or less to a cell mass and acquiring a plurality of light intensity information corresponding to each of a plurality of measuring positions in the cell mass, generating a feature amount from a variation of the acquired plurality of light intensity information, and evaluating quality of the cell mass using the generated feature amount as an index.

BRIEF DESCRIPTION OF DRAWINGS

FIG. 5 is a schematic view for explaining a procedure of deriving the degree of change.

FIG. 7 is a diagram showing image information for explaining a gray level occurrence matrix.

FIG. 8 is a schematic view showing a gray level occurrence matrix.

DESCRIPTION OF EMBODIMENTS

Description of Embodiment of Present Disclosure

Figure 1:
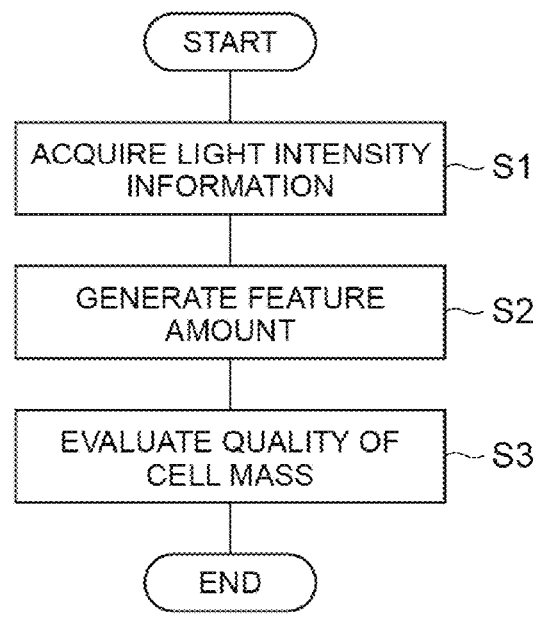
FIG. 1 is a flowchart showing processes of a quality evaluation method.

First, embodiments of the present disclosure will be listed and described.

A quality evaluation method according to one aspect of the present disclosure includes emitting measurement light having a wavelength of 300 nm or more and 2,000 nm or less to a cell mass and acquiring a plurality of light intensity information corresponding to each of a plurality of measuring positions in the cell mass, generating a feature amount from a variation of the acquired plurality of light intensity information, and evaluating quality of the cell mass using the generated feature amount as an index.

In the quality evaluation method, a feature amount is generated from a variation of a plurality of light intensity information corresponding to each of a plurality of measuring positions in the cell mass. Therefore, the feature amount can reflect the relationship between adjacent cells in the cell mass, the relationship between cells at distant positions, and the like. The quality of the cell mass is, for example, an index related to a degree of an ability of cells to aggregate together. Therefore, when the feature amount reflecting the relationship between cells is used as an index, it is possible to evaluate the quality of the cell mass based on the state of the cell mass on the spot regardless of the cause of cell mass occurrence.

The generating may include generating a degree of variance of the plurality of light intensity information as one aspect of the feature amount. In this configuration, it is possible to easily derive a variation of light intensity information using a degree of variance of a plurality of light intensity information as a feature amount.

The generating may include generating a degree of change between the light intensity information at each of the plurality of measuring positions and the light intensity information around each of the plurality of measuring positions as one aspect of the feature amount. In this configuration, the relationship between cells present at positions close to each other in the cell mass is easily reflected in the feature amount.

The generating may include generating a degree of non-uniformity of the plurality of light intensity information in the cell mass as one aspect of the feature amount. The degree of non-uniformity of the light intensity information is an index indicating the locality, variability, or correlation of the distribution of the light intensity information, and corresponds to the pattern or texture of the distribution of the light intensity information. In this configuration, the difference in properties due to the position relationship between cells in the cell mass is easily reflected in the feature amount.

In the generating, the feature amount may be generated from the result obtained by comparing at least one from between the variation and basic statistical amounts of the light intensity information for each region of the cell mass divided into two or more parts. In this configuration, the state of cells for each region in the cell mass is easily reflected in the feature amount.

Details of Embodiment of Present Disclosure

Cell masses can be classified into two types according to the cause of occurrence thereof. One type is a multi-layered cell mass that is a result of increasing the number of cells due to cell division. The other type is a cell mass in which a cell aggregation phenomenon is used and thus a plurality of cells are laminated in multiple layers. In cell masses caused by the aggregation phenomenon, the size and shape of the cell mass can be artificially determined according to the number and arrangement of cells to be aggregated, and the like. Therefore, in cell masses caused by the aggregation phenomenon, it is possible to create cell masses with a large number of layers in one process, instead of gradual multi-layering like cell masses due to cell division.

In the method of evaluating cell masses disclosed in Patent Literature 1, as described above, evaluation is performed based on time-series images of cell masses. Therefore, it may not be suitable for evaluating the quality of cell masses that are multi-layered in a short time, such as cell masses caused by the aggregation phenomenon. In addition, even if the cell mass is based on cell division, it is difficult to acquire a time-series image when the quality of the cell mass that has already been multi-layered is evaluated.

The present disclosure provides a quality evaluation method in which it is possible to evaluate the quality of a cell mass based on the state of the cell mass on the spot regardless of the cause of cell mass occurrence.

Specific examples of the quality evaluation method according to the present disclosure will be described below with reference to the drawings. It should be noted that the present invention is not limited to these examples, but is indicated by the scope of the claims, and is intended to include meanings equivalent to the scope of the claims and all modifications within the scope of the claims.

As shown in FIG. 1, in the quality evaluation method according to one embodiment, a plurality of light intensity information corresponding to each of a plurality of measuring positions in the cell mass are acquired (Step S1). A feature amount is generated from a variation of the acquired plurality of light intensity information (Step S2). The quality of the cell mass is evaluated using the generated feature amount (Step S3). In this specification, the cell mass (spheroid) is a cluster in which a plurality of cells are aggregated due to a cell aggregation phenomenon or a cluster in which a plurality of cells are divided by cell division. The cell mass includes various forms of cells such as a 2D cluster and a 3D cluster. As an example, the cell mass may be a cluster in which about 10,000 to 50,000 cells having a diameter of about 10 μm are aggregated. The cells contained in the cell mass are composed of stem cells collected from animals or humans, stem cells prepared based on cells collected from animals or humans, or cells differentiated from stem cells. A plurality of cells may be mixed in one cell mass. In addition, the "quality" of the cell mass indicates the "activity," "degree of activity," or "active function" of the cell mass. The "activity," "degree of activity," or "active function" is an index related to a cell lineage ability, a cell aggregation ability, a cell mass aggregation ability, a tissue regeneration ability in living bodies, safety in living bodies, or the like. Here, the cell lineage ability is an ability to maintain a life cycle such as cell proliferation, an ability to become specific tissue cells, an ability to maintain functions required as cells, or the like.

Figure 2:
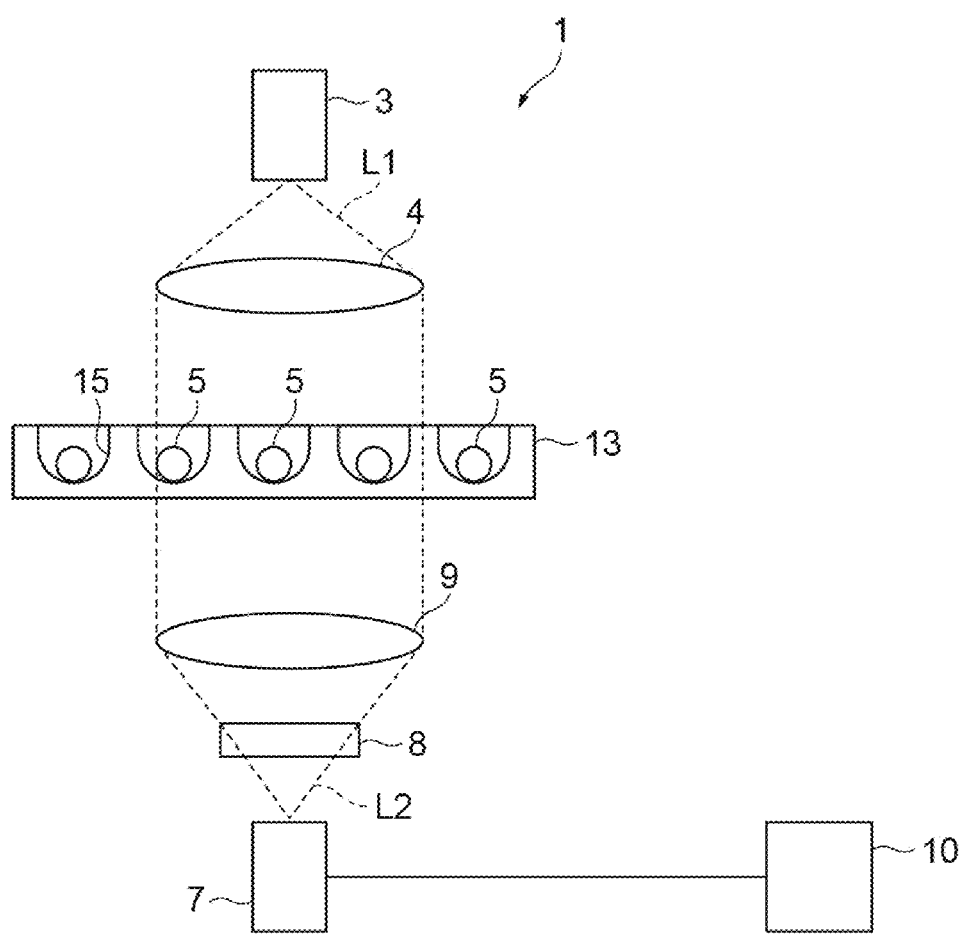
FIG. 2 is a schematic configuration diagram showing an example of a quality evaluation device.

First, a configuration of a quality evaluation device that acquires light intensity information will be described. FIG. 2 is a schematic configuration diagram showing an example of a quality evaluation device. A quality evaluation device 1 includes a light source 3, a lens 4, a 2D sensor 7, a bandpass filter 8 and a lens 9. The 2D sensor 7, the bandpass filter 8, and the lens 9 face the light source 3 and the lens 4 with cell masses 5 to be evaluated therebetween. As an example, the cell mass 5 may be accommodated in a microplate 13 in which a plurality of wells 15 are arranged two-dimensionally. In this case, the quality evaluation device 1 may have a mounting table on which the microplate 13 is mounted. The cell masses 5 are accommodated in the wells 15 of the microplate 13 together with a culture medium.

The light source 3 and the lens 4 are arranged at positions facing one surface (upper surface in the illustrated example) of the microplate 13. The light source 3 emits measurement light L1 toward the cell mass 5. The measurement light L1 has a wavelength included in, for example, a wavelength range of 300 nm or more and 2,000 nm or less. As an example, the light source 3 may be a halogen lamp, but the type of light source is not particularly limited. As described above, the cell mass 5 is an aggregated cell mass. Therefore, light incident on the cell mass 5 is likely to scatter. Therefore, regarding the measurement light L1, near infrared light which is less scattered by the cell mass 5 and has a wavelength in which an amount of absorption by a culture medium is small may be used. Specifically, measurement light included in a wavelength range of 800 nm or more and 1,850 nm or less may be used. The measurement light L1 output from the light source 3 passes through the cell mass 5 accommodated in the microplate 13 via the lens 4. Then, some of the measurement light L1 is output as transmitted light L2. The lens 4 is a condensing lens that condenses measurement light L1 from the light source 3 or a condensing lens that performs collimation.

The 2D sensor (light receiving unit) 7 detects transmitted light L2 that passes through each of a plurality of measuring positions in the cell masses 5. The 2D sensor 7 has a light receiving surface. On the light receiving surface, a plurality of light receiving elements are arranged two-dimensionally. Each light receiving element receives light and converts it into an electrical signal. As an example, the 2D sensor 7 may be a camera including a 2D element such as InGaAs or HgCdTe. For example, the 2D sensor 7 acquires an image formed by the transmitted light L2 that passed through the cell mass 5. That is, image information of the cell mass 5 acquired by the 2D sensor 7 includes intensity information of the transmitted light L2 for each position in the cell mass 5. In the following description, "pixel" may include the meaning of "position."

Figure 3:
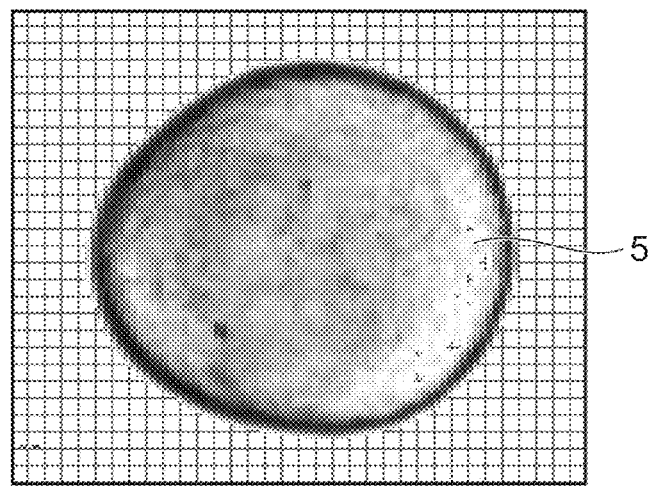
FIG. 3 shows an example of information on a cell mass image acquired by a 2D sensor.

FIG. 3 shows an example of image information of cell masses acquired by the 2D sensor. The image information shown in FIG. 3 reflects the intensity of the transmitted light L2 when the measurement light L1 is emitted to the cell mass 5 in gray scales. In the image, the part shown in dark gray is a part of the cell mass 5 having low transmittance, and the part shown in light gray is a part of the cell mass 5 having high transmittance.

Here, as shown in FIG. 2, the transmitted light L2 that has passed through the cell mass 5 is incident on the 2D sensor 7 via the lens 9 and the bandpass filter 8. In one aspect, the lens 9 is an objective lens. The bandpass filter 8 allows light having a specific wavelength within the transmitted light L2 to pass therethrough and to be input to the 2D sensor 7. Here, although an example in which the bandpass filter 8 is arranged between the lens 9 and the 2D sensor 7 is shown, the bandpass filter 8 may be provided at any position between the light source 3 and the 2D sensor 7. In addition, when it is desired to acquire image information separately not only for a specific wavelength within the transmitted light L2 but also for a plurality of wavelengths, a spectroscope may be provided in place of the bandpass filter 8. A signal indicating the intensity of the transmitted light L2 acquired by the 2D sensor 7 (that is, image information) is output to an analysis unit 10.

The analysis unit 10 is composed as a computer including hardware. The hardware includes a central processing unit (CPU), a random access memory (RAM) and a read only memory (ROM) which are main storage devices, and a communication module that communicates with other devices such as a 2D sensor. In addition, the hardware includes an auxiliary storage device such as a hard disk. Here, when these components are operated, functions of the analysis unit 10 are exhibited.

The analysis unit 10 acquires light intensity information for each of a plurality of measuring positions in the cell masses 5. The light intensity information is a concept including a transmitted light intensity, a diffuse reflection light intensity, and a fluorescence intensity acquired when the measurement light L1 is emitted to the cell mass 5. In addition, the light intensity information is a concept including transmittance and absorbance obtained based on the transmitted light intensity, the diffuse reflection light intensity, and the fluorescence intensity. In addition, when light intensity information is acquired using the measurement light L1 with a plurality of wavelengths with respect to the same position of the cell mass 5, information obtained by combining light intensity information at a plurality of wavelengths is also included in the light intensity information. For example, the difference between the transmitted light intensities at a plurality of wavelengths is also included in the light intensity information.

As an example, the analysis unit 10 acquires a transmitted light intensity based on a signal input from the 2D sensor 7. In addition, in addition to measurement of a transmitted light intensity related to the cell mass 5, the analysis unit 10 acquires in advance a light intensity obtained when measurement light L1 from the light source 3 is incident on the 2D sensor 7 in the absence of the cell mass 5. Then, the analysis unit 10 may determine transmittance of the transmitted light L2 derived from the cell mass 5 based on the light intensity and the transmitted light intensity related to the cell mass 5.

In addition, the analysis unit 10 acquires a feature amount based on the variation of the light intensity information acquired for each position. The analysis unit 10 evaluates the quality of the cell mass 5 using the acquired feature amount as an index. The evaluation result may be output from the analysis unit 10 via an output device such as a monitor or a printer. The "variation" of light intensity information may be a state of deviation of light intensity information in a plane in which a cell mass is observed in a specific direction, a state of deviation of light intensity information in a specific cross section of a cell mass, or a state of deviation of light intensity information when a cell mass is captured three-dimensionally. Therefore, the feature amount based on the variation may be a degree of variance, a degree of change, a degree of non-uniformity, or the like in the light intensity information in the cell mass.

Hereinafter, a case in which a feature amount is generated from a variation of light intensity information, and the quality of the cell mass can be evaluated using the feature amount as an index will be described with reference to first to fifth examples. Here, the first to fifth examples are examples of the quality evaluation method, and the present disclosure is not limited to the first to fifth examples.

First Example

In the first example, regarding the feature amount indicating a variation of light intensity information in the cell mass, the variance (variance value) of light intensity information is used. The variance is an example of an index indicating a degree of variance of light intensity information. In the first example, first, an evaluation criterion for cell mass quality is set. For setting of the evaluation criterion, normal cell masses cultured under normal conditions and cell masses with a reduced degree of activity (an example of quality) are used. As an example, the normal cell masses are cell masses cultured for 2 days using a Dulbecco's modified eagle medium (DMEM). The cell masses with a reduced degree of activity are cell masses cultured for 2 days using a DMEM to which 5 volume % of dimethyl sulfoxide (DMSO) is added. Cells constituting a cell mass to be evaluated are normal human dermal fibroblasts (NHDF).

When the evaluation criterion is set, first, the quality evaluation device 1 is used to acquire light intensity information of each of normal cell masses and cell masses with a reduced degree of activity. As an example, the light intensity information is transmittance of transmitted light acquired from the image information generated by the 2D sensor.

Subsequently, the variance of a plurality of transmittances acquired for each pixel is obtained from each of the normal cell masses and the cell masses with a reduced degree of activity. Then, based on the obtained variance, a value of the variance is set as an evaluation criterion used for discriminating between the normal cell masses and the cell masses with a reduced degree of activity.

Figure 4:
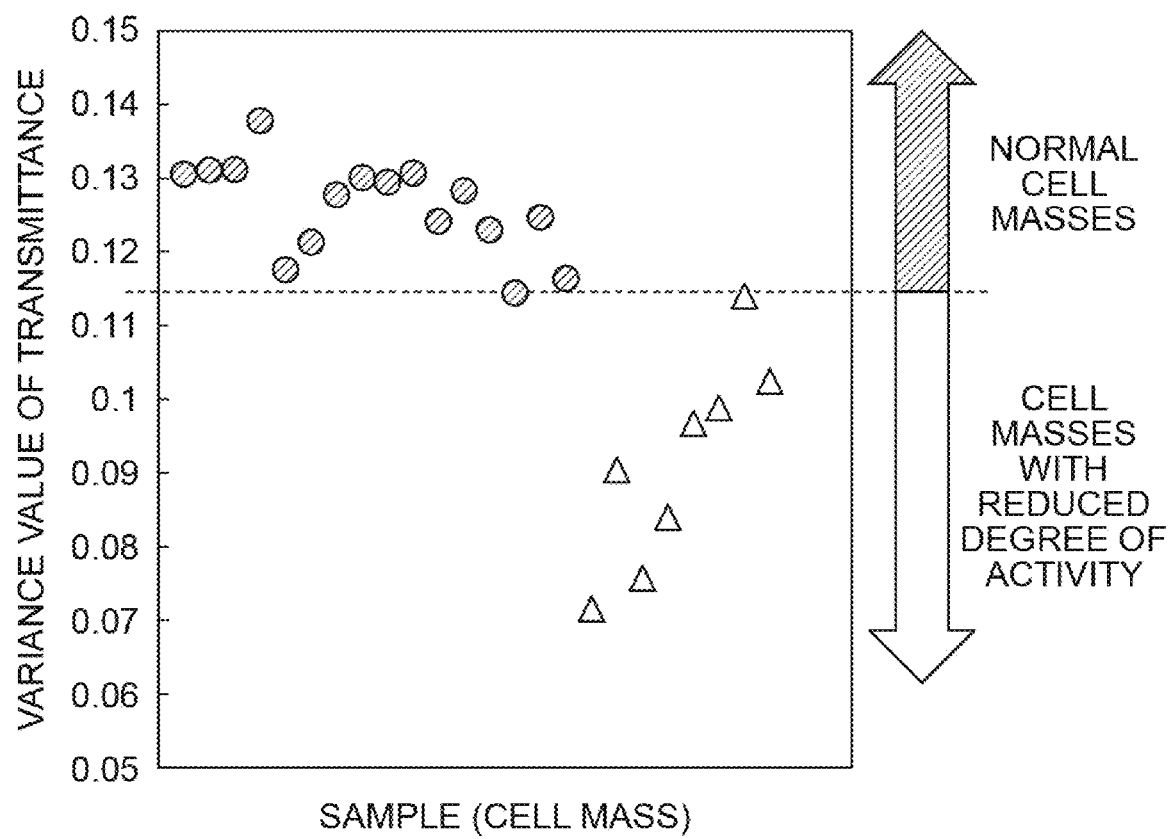
FIG. 4 is a graph showing variances of transmittance of normal cell masses and cell masses with a reduced degree of activity.

FIG. 4 is a graph showing variances of transmittances of normal cell masses and cell masses with a reduced degree of activity. As shown in FIG. 4, the normal cell masses have a higher variance value than the cell masses with a reduced degree of activity. Therefore, the normal cell masses and the cell masses with a reduced degree of activity can be discriminated using the variance of transmittance. In the drawing, a dotted line indicating the variance as an evaluation criterion is exemplified between the minimum value among the variances of the normal cell masses and the maximum value among the variances of the cell masses with a reduced degree of activity. When the quality of a cell mass whose quality is unknown is evaluated, first, the variance of transmittance of the cell mass is acquired. Then, the quality of the cell mass can be evaluated by comparing the variance of the transmittance with a set evaluation criterion. That is, when the cell mass has a higher variance value than the evaluation criterion, the quality of the cell mass can be evaluated as being the same as that of the normal cell mass. When the cell mass has a lower variance value than the evaluation criterion, the quality of the cell mass can be evaluated as being the same as that of the cell mass with a reduced degree of activity. Here, in order to increase the evaluation reliability, the evaluation criterion may be arbitrarily set. For example, in order to reliably select only cell masses having the same quality as the normal cell mass and prevent cell masses with a reduced degree of activity from being included, the evaluation criterion of the variance value may be set to be larger than the shown evaluation criterion.

Second Example

In the second example, a degree of change in light intensity information is used as the feature amount indicating a variation of light intensity information in the cell mass. The degree of change in light intensity information is a value based on a difference or differentiation between light intensity information at each of a plurality of measuring positions and light intensity information at the surrounding measuring position. In the second example, first, an evaluation criterion for cell mass quality is set. For setting of the evaluation criterion, normal cell masses cultured under normal conditions and cell masses with a reduced degree of activity are used. As an example, the normal cell masses are cell masses cultured for 2 days using a DMEM. The cell masses with a reduced degree of activity are cell masses cultured for 2 days using a DMEM to which 5 volume % of DMSO is added. In this example, cells constituting a cell mass to be evaluated are NHDF.

When the evaluation criterion is set, first, the quality evaluation device is used to acquire light intensity information of each of the normal cell masses and cell masses with a reduced degree of activity. As an example, the light intensity information is transmittance of transmitted light acquired from the image information generated by the 2D sensor.

Subsequently, the degree of change in transmittance is obtained from each of the normal cell masses and the cell masses with a reduced degree of activity. Then, based on each of the obtained degrees of change in transmittance, a value of the degree of change in transmittance as an evaluation criterion used for discriminating between the normal cell masses and the cell masses with a reduced degree of activity is set.

Figure 5:
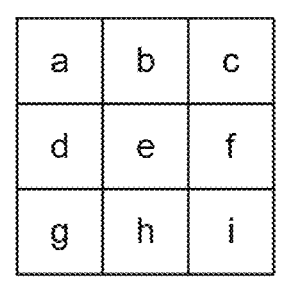

FIG. 5 is a schematic view for explaining a procedure of deriving the degree of change. In the drawing, some pixels of image information acquired by the 2D sensor are shown, and characters a to i are assigned to respective pixels. As an example, the degree of change in transmittance in an arbitrary pixel is defined as a sum of absolute values of differences between the transmittance in an arbitrary pixel and the transmittance in other pixels therearound. In the illustrated example, the sum of absolute values of differences between the transmittance in an arbitrary pixel and the transmittance in other pixels adjacent to the arbitrary pixel is a degree of change in transmittance in the arbitrary pixel. For example, when the degree of change in transmittance in the pixel e is set as T, T is assigned by the following formula. Here, $T(a)$ to $T(i)$ each indicate the transmittance in the pixel a to the pixel i.

$$T=|T(a)-T(e)|+|T(b)-T(e)|+ \ldots +|T(h)-T(e)|+|T(i)-T(e)|$$

The sum of the degrees of change in all pixels in the cell mass is defined as the degree of change in transmittance of the cell mass.

Figure 6:
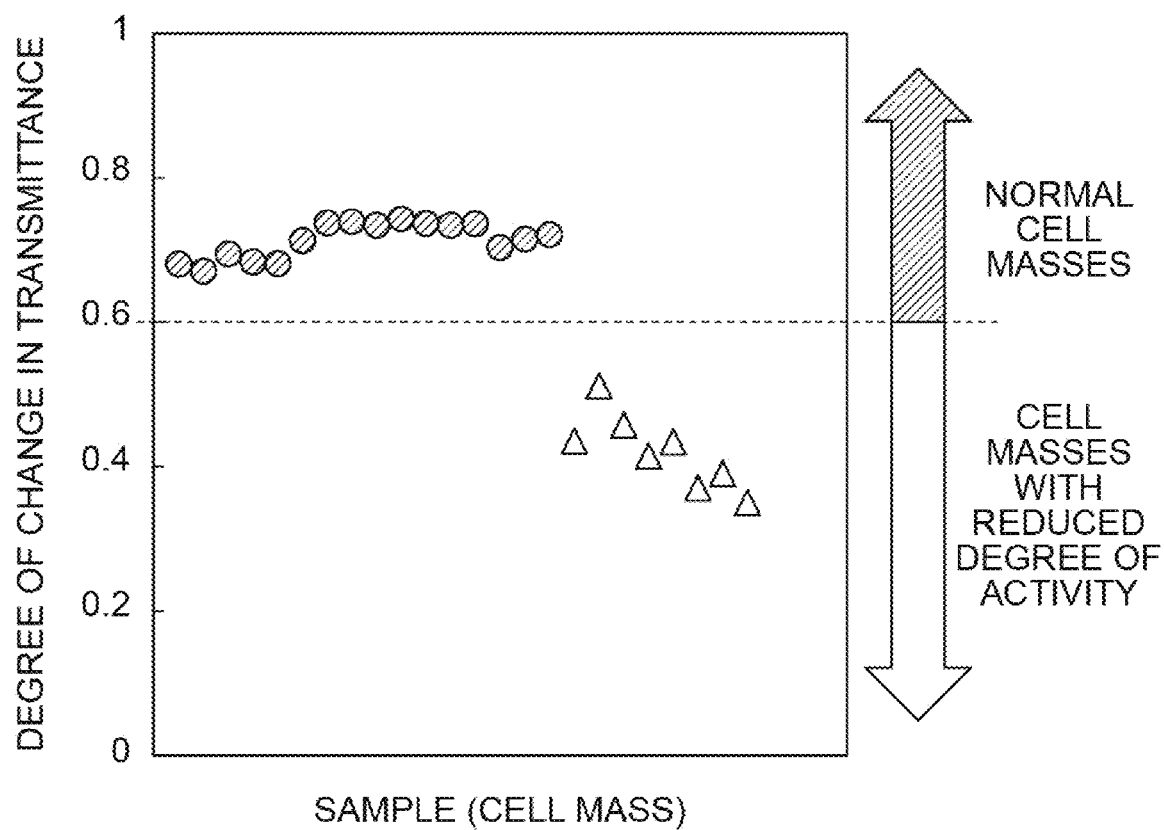
FIG. 6 is a graph showing values of the degree of change of each of normal cell masses and cell masses with a reduced degree of activity.

FIG. 6 is a graph showing values of the degree of change of each of normal cell masses and cell masses with a reduced degree of activity. As shown in FIG. 6, the normal cell masses have a higher value of the degree of change than the cell masses with a reduced degree of activity. Therefore, the normal cell masses and the cell masses with a reduced degree of activity can be discriminated using the value of the degree of change in transmittance. In the drawing, a dotted line indicating the value of the degree of change as an evaluation criterion is exemplified. The dotted line is shown between the minimum value among values of the degree of change in transmittance of the normal cell masses and the maximum value among values of the degree of change in transmittance of the cell masses with a reduced degree of activity. When the quality of a cell mass whose quality is unknown is evaluated, first, the degree of change in transmittance of the cell mass is acquired. Then, the quality of the cell mass can be evaluated by comparing the value of the degree of change in transmittance with a set evaluation criterion. That is, when the cell mass has a higher value of the degree of change in transmittance than the evaluation criterion, the quality of the cell mass can be evaluated as being the same as that of the normal cell mass. In addition, when the cell mass has a lower value of the degree of change in transmittance than the evaluation criterion, the quality of the cell mass can be evaluated as being the same as that of the cell mass with a reduced degree of activity. Here, in order to increase the evaluation reliability, the evaluation criterion may be arbitrarily set. For example, in order to select only cell masses having the same quality as the normal cell mass and prevent cell masses with a reduced degree of activity from being included, the evaluation criterion of the value of the degree of change in transmittance may be set to be larger than the shown evaluation criterion.

Third Example

In the third example, the degree of non-uniformity of light intensity information is used as the feature amount indicating a variation of light intensity information in the cell mass. As an example, a feature amount based on texture analysis is used as information reflecting the degree of non-uniformity of light intensity information. The feature amount based on the texture analysis comprehensively reflects properties of 2D distribution such as the shape, distribution, density, and direction indicated by respective pixels of the image information. That is, the feature amount based on the texture analysis can reflect distribution features such as periodicity, uniformity, non-uniformity, locality, variability, and correlation of information in respective pixels of the image information. In this example, as an example of the texture analysis, analysis using a gray level occurrence matrix is used, but for example, other methods such as structural analysis may be used.

In this example, first, an evaluation criterion for cell mass quality is set. For setting of the evaluation criterion, normal cell masses cultured under normal conditions and cell masses with a reduced degree of activity are used. As an example, the normal cell masses are cell masses cultured for 2 days using a DMEM. The cell masses with a reduced degree of activity are cell masses cultured for 2 days using a DMEM to which 5 volume % of DMSO is added. Cells constituting a cell mass to be evaluated are, for example, NHDF.

When the evaluation criterion is set, first, the quality evaluation device is used to acquire light intensity information of each of the normal cell masses and cell masses with a reduced degree of activity. As an example, the light intensity information is transmittance of transmitted light acquired from the image information generated by the 2D sensor.

Figure 7:
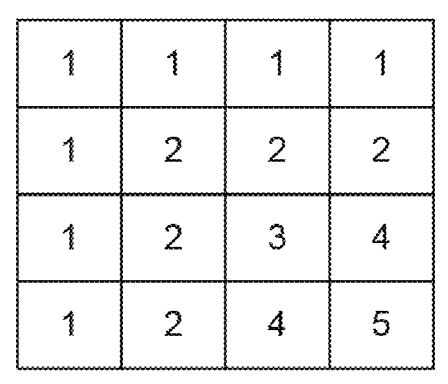

Subsequently, a gray level occurrence matrix reflecting the transmittance is obtained for each of the normal cell masses and the cell masses with a reduced degree of activity. FIG. 7 is a schematic view for explaining image information processed in order to generate a gray level occurrence matrix. FIG. 8 is a schematic view for explaining a gray level occurrence matrix. In the example in FIG. 7, some pixels of cell mass image information are schematically shown. Each pixel is associated with a value (gray level) obtained by normalizing the transmittance for each pixel in a plurality of stage (5 stages in the illustrated example). FIG. 8 shows a gray level occurrence matrix generated based on the image information of the example in FIG. 7.

In the gray level occurrence matrix, the gray level value (i) of the pixel captured as the center is treated as that of the row. The number of pixels adjacent to the pixel captured as the center is totaled for each gray level value (j) of adjacent pixels. For example, in FIG. 7, the pixel having a gray level value of 5 is only the lower right pixel. That is, in the case in which the pixel gray level captured as the center is 5 (that is, the row of i=5), only the lower right pixel may be focused on. When the row of i=5 is described, pixels adjacent to the lower right pixel are three upper, upper left, and left pixels, and the gray levels of these three pixels do not include 1, 2, and 5. Therefore, the values in the row of i=5 and the columns of j=1, 2, and 5 in the gray level occurrence matrix are 0. The gray scales of three pixels adjacent to the lower right pixel are 4, 3, and 4. That is, there are one pixel having a gray scale of 3 and two pixels having a gray scale of 4. Therefore, the values in the row of i=5 and the columns of j=3 and 4 in the gray level occurrence matrix are 1 and 2.

The feature amount is derived based on texture analysis from the obtained gray level occurrence matrix. The feature amount based on the texture analysis comprehensively expresses properties of 2D distribution such as the shape, distribution, density, and direction expressed by the image information. The feature amount can be expressed as "energy," "uniformity," "entropy," "dissimilarity," "contrast," "homogeneity," "inverse difference moment," "maximum probability" or the like. As an example, the formulae for deriving "Entropy," "Energy," "Dissimilarity," and "Homogeneity" when each component of the gray level occurrence matrix is represented by $P_{i,j}$ are shown below. Here, in this example, as an example, energy is used as the feature amount.

$$\text{Entropy} = -\sum_{i,j} P_{i,j} \log P_{i,j} \quad \text{[Math. 1]}$$

$$\text{Energy} = \sum_{i,j} P_{i,j}^2 \quad \text{[Math. 2]}$$

$$\text{Dissimilarity} = \sum_{i,j} P_{i,j}|i-j| \quad \text{[Math. 3]}$$

$$\text{Homogeneity} = \sum_{i,j} \frac{P_{i,j}}{1+|i-j|} \quad \text{[Math. 4]}$$

Figure 9:
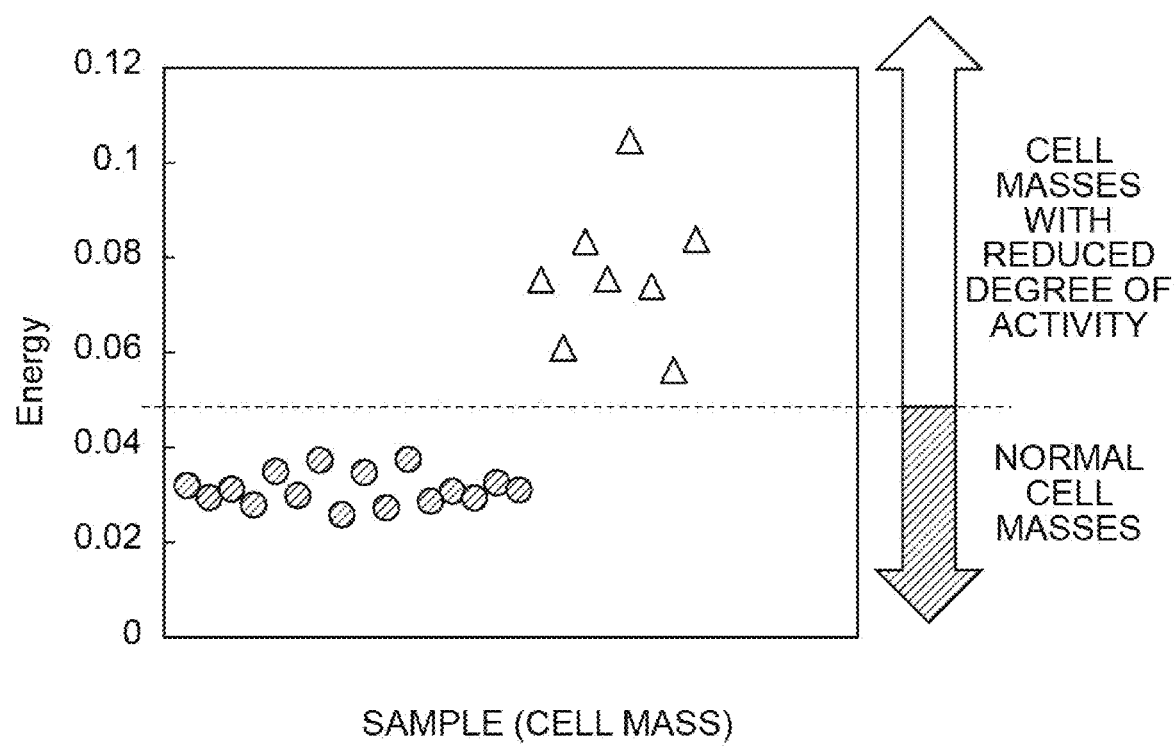
FIG. 9 is a graph showing energies of each of normal cell masses and cell masses with a reduced degree of activity.

Then, based on each of the obtained energies, the value of energy is set as an evaluation criterion used for discriminating between the normal cell masses and the cell masses with a reduced degree of activity. FIG. 9 is a graph showing energies of each of the normal cell masses and the cell masses with a reduced degree of activity. As shown in FIG. 9, the normal cell masses have a lower energy value than the cell masses with a reduced degree of activity. Therefore, the normal cell masses and the cell masses with a reduced degree of activity can be discriminated using the energy. In the drawing, a dotted line indicating the value of energy as an evaluation criterion is exemplified. The dotted line is shown between the maximum value among energies of the normal cell masses and the minimum value among energies of the cell masses with a reduced degree of activity.

When the quality of a cell mass whose quality is unknown is evaluated, first, the value of energy of transmittance of the cell mass is acquired. Then, the quality of the cell mass can be evaluated by comparing the value of energy with a set evaluation criterion. That is, when the cell mass has lower energy than the evaluation criterion, the quality of the cell mass can be evaluated as being the same as that of the normal cell mass. In addition, when the cell mass has higher energy than the evaluation criterion, the quality of the cell mass can be evaluated as being the same as that of the cell mass with a reduced degree of activity. Here, in order to increase the evaluation reliability, the evaluation criterion may be arbitrarily set. For example, in order to select only cell masses having the same quality as the normal cell mass and prevent cell masses with a reduced degree of activity from being included, the evaluation criterion of the value of energy may be set to be lower than the shown evaluation criterion.

Fourth Example

In the fourth example, as the feature amount indicating a variation of light intensity information in the cell mass, the result obtained by comparing at least one from between a variation and basic statistical amounts of the light intensity information for each region of the cell mass is used. Hereinafter, a case in which the quality of the cell mass can be evaluated using light intensity information will be described. In this example, normal cell masses cultured under normal conditions and cell masses with a reduced degree of activity (that is, quality) are used. As an example, the normal cell masses are cell masses cultured for 2 days using a DMEM. The cell masses with a reduced degree of activity are cell masses in which cells with different properties are mixed depending on culture conditions and the like. NHDFs are used as cells constituting the cell mass.

The quality evaluation device is used to acquire light intensity information of each of the normal cell masses and the cell masses with a reduced degree of activity. As an example, the light intensity information is transmittance of transmitted light acquired from the image information generated by the 2D sensor.

Figure 10:
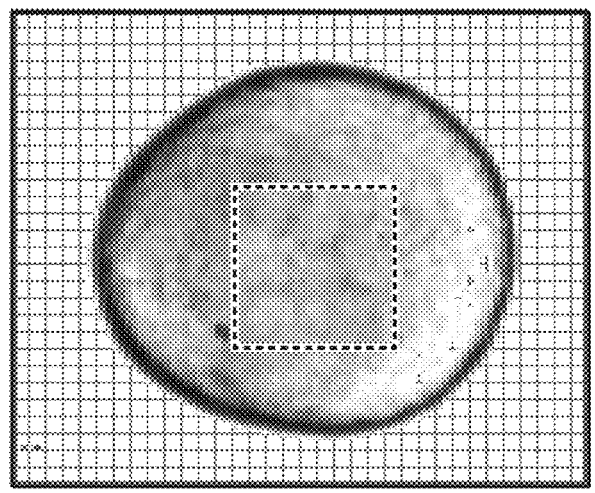
FIG. 10 is a schematic view for explaining an example in which a cell mass image is divided into two parts.

Subsequently, for each of the normal cell masses and the cell masses with a reduced degree of activity, the image is divided into two or more regions. FIG. 10 is a schematic view for explaining an example in which a cell mass image is divided into two parts. In the example in FIG. 10, the region in the cell mass is divided into a central part (indicated by a dotted line in the drawing) and the outer peripheral part. In the illustrated example, the central part is a square composed of sides with a length of about half of the diameter of the cell mass. Here, the central part may be a circle having a radius with a length of about half of the radius of the cell mass. The outer peripheral part may be a part obtained by removing the central part from the cell mass.

Next, in the central part and the outer peripheral part, at least one from between the variation and basic statistical amounts of the light intensity information of pixels included in each region are obtained as "light intensity information in regions." For example, the basic statistical amount is an index indicating a characteristic, trend or the like of the light intensity information in the region as a whole, and as an example, an average value, a mode value, a median value, or the like may be used.

Figure 11:
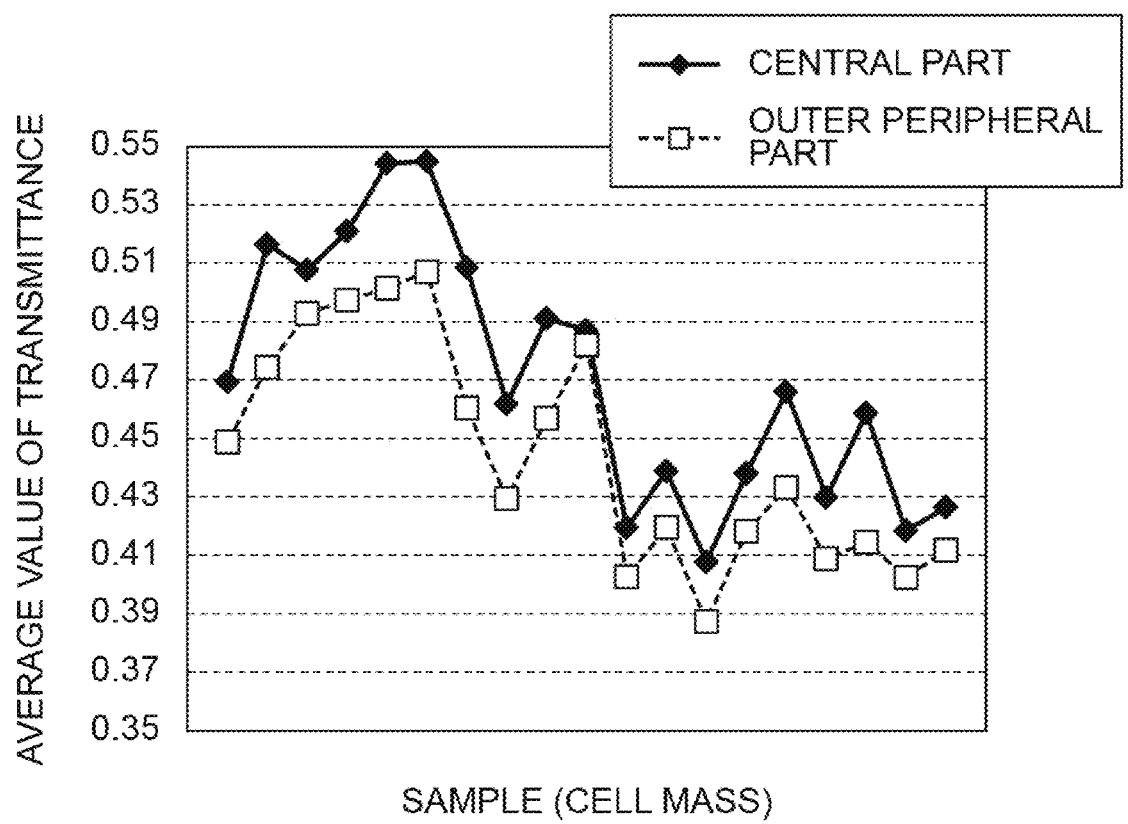
FIG. 11 is a graph showing the results of evaluation of cell masses using "light intensity information in regions."
Figure 12:
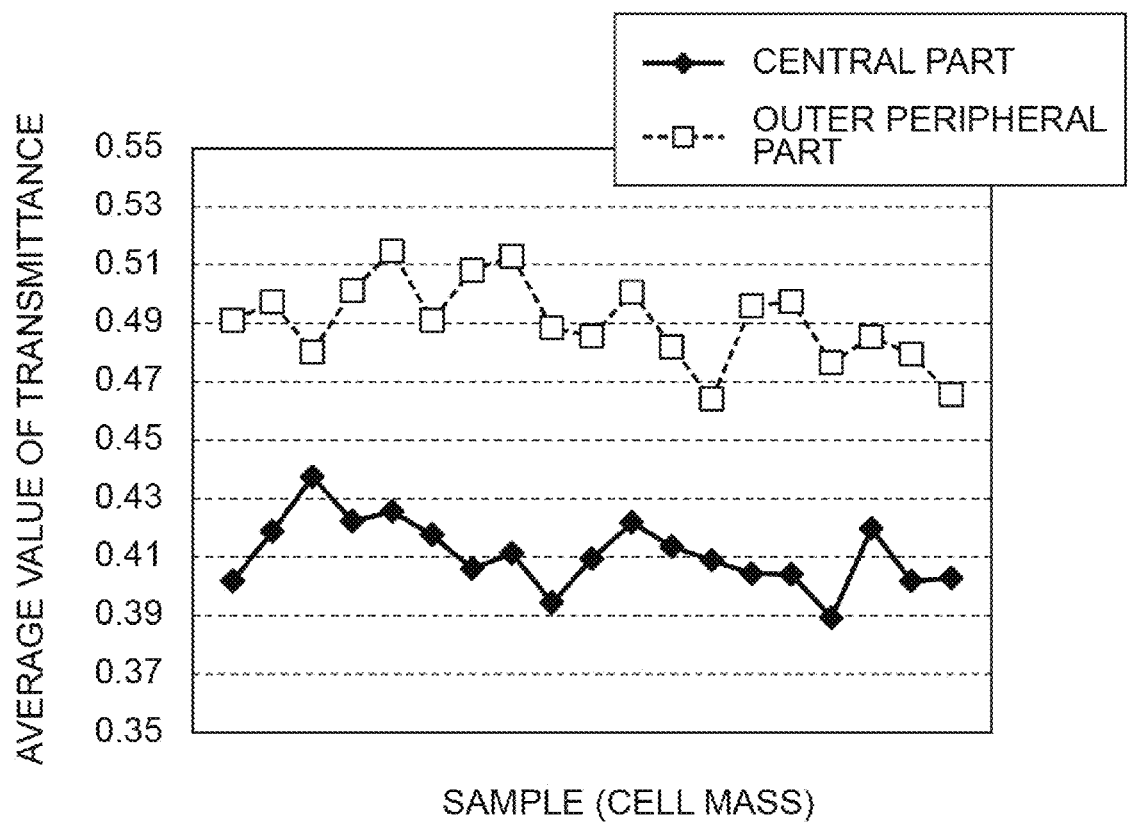
FIG. 12 is a graph showing the results of evaluation of cell masses using "light intensity information in regions."

Then, the obtained "light intensity information in regions" are compared with each other and the comparison result is obtained. The comparison result shows the variation of "light intensity information in regions" in the cell mass. FIG. 11 shows the comparison results of normal cell masses when an average value of transmittances is used as "light intensity information in regions." As shown in FIG. 11, in the normal cell masses, the average transmittance of the outer peripheral part is smaller than the average transmittance of the central part. FIG. 12 shows the comparison results of the cell masses with a reduced degree of activity when an average value of transmittances is used as "light intensity information in regions." As shown in FIG. 12, in the cell masses with a reduced degree of activity, the average transmittance of the outer peripheral part is larger than the average transmittance of the central part. When the quality of a cell mass whose quality is unknown is evaluated, first, a result obtained by comparing the average transmittance of the central part with the average transmittance of the outer peripheral part in the cell mass is acquired. Then, based on the comparison results, the quality of the cell mass can be evaluated. That is, when the average transmittance of the outer peripheral part is smaller than the average transmittance of the central part, the cells can be evaluated as normal cells having favorable quality.

Figure 13:
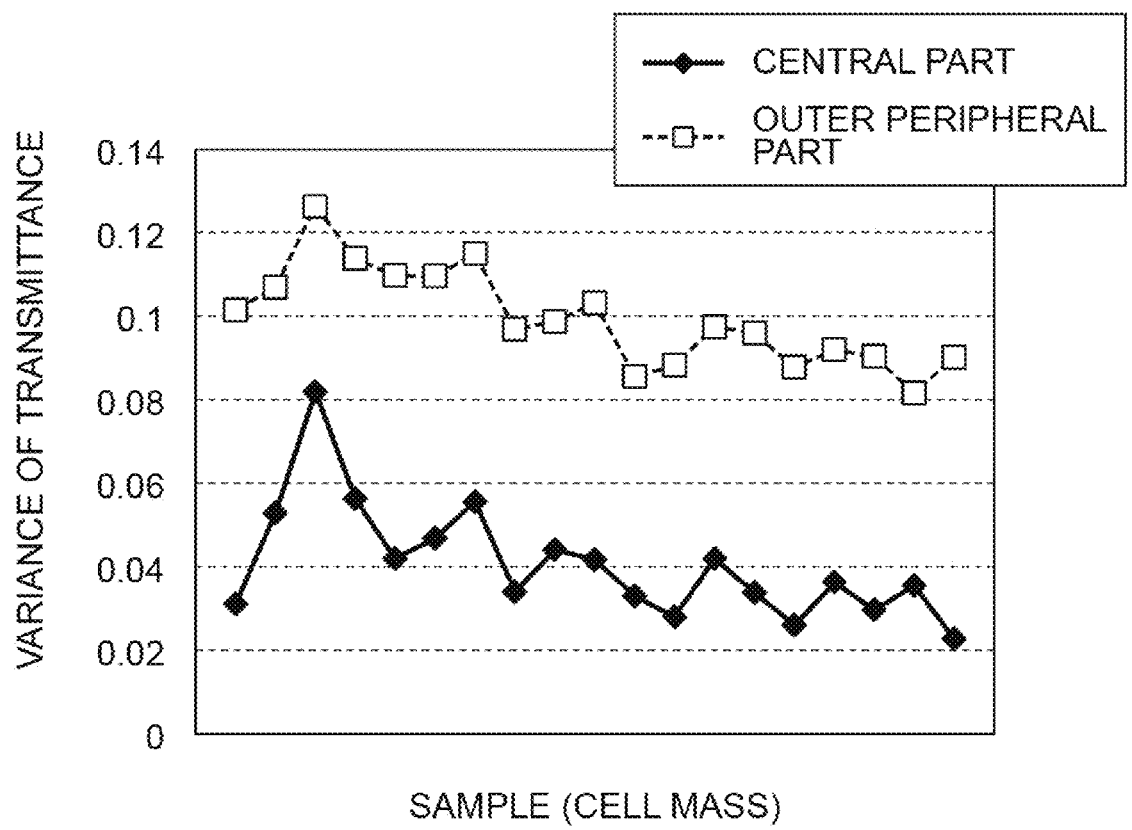
FIG. 13 is a graph showing the results of evaluation of cell masses using "light intensity information in regions."
Figure 14:
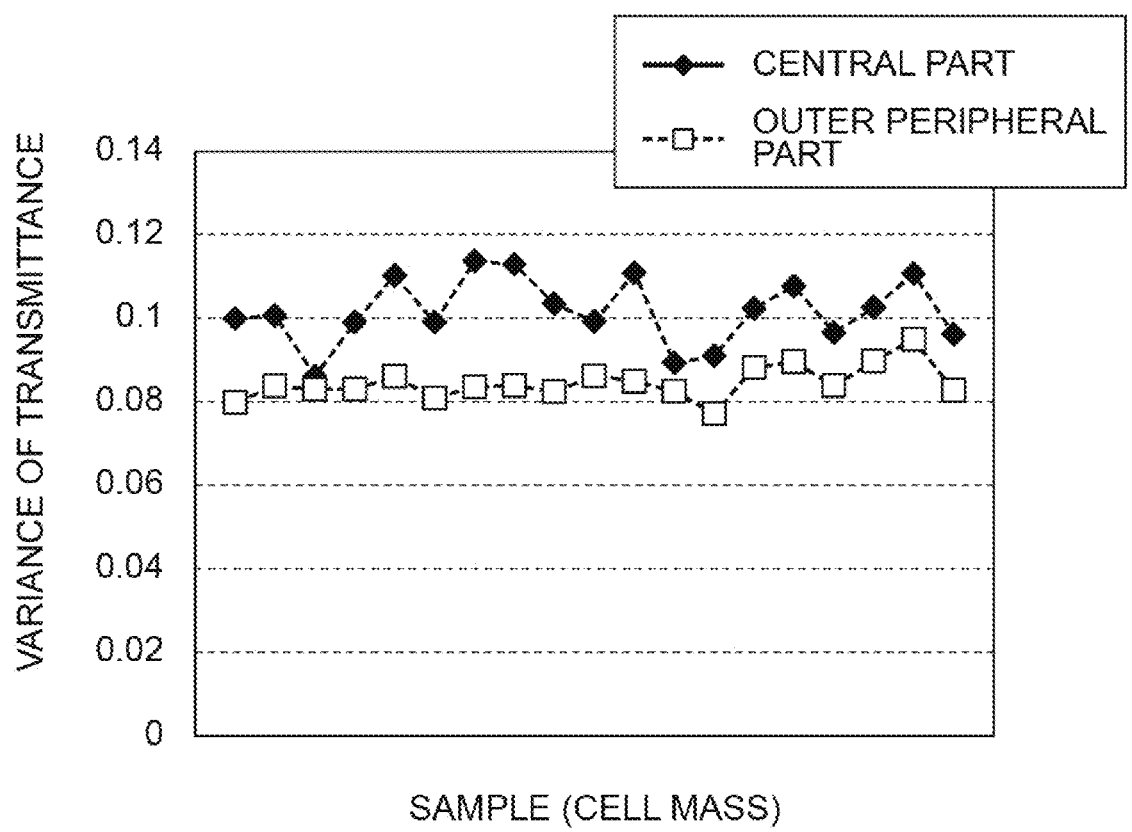
FIG. 14 is a graph showing the results of evaluation of cell masses using "light intensity information in regions."

FIG. 13 shows the comparison results of normal cell masses when the variance of transmittance is used as light intensity information in regions. As shown in FIG. 13, in the normal cell masses, the variance of transmittance of the outer peripheral part is larger than the variance of transmittance of the central part. FIG. 14 shows the comparison results of cell masses with a reduced degree of activity when the variance of transmittance is used as light intensity information in regions. As shown in FIG. 14, in the cell masses with a reduced degree of activity, the variance of transmittance of the outer peripheral part is smaller than the variance of transmittance of the central part. When the quality of a cell mass whose quality is unknown is evaluated, first, a result obtained by comparing the variance of transmittance of the central part with the variance of transmittance of the outer peripheral part in the cell mass is acquired. Then, based on the comparison results, the quality of the cell mass can be evaluated. That is, when the variance of transmittance of the outer peripheral part is larger than the variance of transmittance of the central part, the cells can be evaluated as normal cells having favorable quality.

Here, in the examples in FIG. 11 to FIG. 14, "light intensity information in regions" are compared with each other using the average value or the variance, but when "light intensity information in regions" are compared with each other, other basic statistical amounts may be used.

Fifth Example

In the fifth example, the quality is evaluated based on a plurality of combinations of feature amounts indicating a variation of light intensity information in the cell mass. In this example, the quality is evaluated by a so-called machine learning. As an example, a regression equation including a plurality of feature amounts as explanatory variables and quality as an objective variable is generated. In generation of regression equations, for example, LASSO regression is used so that the influence of variable collinearity is minimized.

In this example, normal cell masses cultured under normal conditions and cell masses with a reduced degree of activity (that is, quality) are used. As an example, the normal cell masses are cell masses cultured using a DMEM for 2 days to 4 days. The cell masses with a reduced degree of activity include a cell mass cultured using a DMEM to which 1 volume % of DMSO is added for 2 days to 4 days (Sample 1), a cell mass cultured using a DMEM to which 5 volume % of DMSO is added for 2 days to 4 days (Sample 2), a cell mass cultured using a DMEM to which AG490 is added for 2 days to 4 days (Sample 3), a cell mass cultured using a DMEM to which Rock Inhibitor is added for 2 days to 4 days (Sample 4), a cell mass cultured by serum-free culture for 2 days to 4 days (Sample 5), and a cell mass cultured using passaging cells for 2 days to 4 days (Sample 6). NHDFs are used as cells constituting the cell mass to be evaluated.

The quality evaluation device is used to acquire light intensity information of each of the normal cell masses and the cell masses with a reduced degree of activity. As an example, the light intensity information is transmittance of transmitted light acquired from the image information generated by the 2D sensor. In this example, when a spectroscope is used in place of the bandpass filter, the transmittance is acquired for each of 65 wavelengths included in a wavelength range of 300 nm or more and 2,000 nm.

The variance of transmittance for each pixel at each wavelength is obtained from each of the normal cell masses and the cell masses with a reduced degree of activity. The variance is acquired when a culture time of 2 days has elapsed, when a culture time of 3 days has elapsed, and when a culture time of 4 days has elapsed. The number of feature amounts acquired accordingly is 3×65×2 with 3 representing the culture time, 65 the wavelength, and 2 the transmittance.

In addition, the degree of change in transmittance is obtained when a culture time of 2 days has elapsed, when a culture time of 3 days has elapsed, and when a culture time of 4 days has elapsed. The number of feature amounts acquired accordingly is 3×65×1 with 3 representing the culture time and 65 the wavelength. The degree of change in transmittance can be obtained in the same manner as in the third example.

In addition, the feature amount based on texture analysis is obtained when a culture time of 2 days has elapsed, when a culture time of 3 days has elapsed, and when a culture time of 4 days has elapsed. The feature amount based on the texture analysis may be, for example, energy, and can be obtained in the same manner as in the fourth example. The number of feature amounts acquired accordingly is 3×65×1 with 3 representing the culture time and 65 the wavelength.

In addition, the feature amount is obtained from at least one from between the variation and basic statistical amounts of the light intensity information for each region of the cell mass. As an example, the cell mass is divided into five regions, and the variance of transmittance is obtained for each of the divided regions. The image information of the cell mass can be divided by a plurality of methods. As an example, the image information of the cell mass may be divided by a method of evenly dividing the cell mass into 5 regions in the circumferential direction based on the center of the cell mass, a method of dividing the cell mass into 5 regions in the longitudinal direction, or method of dividing the cell mass into 5 regions in the lateral direction. The number of feature amounts acquired accordingly is 3×65×(5×3)×2 with 3 representing the culture time, 65 the wavelength, 3 the method of performing division into 5 regions, and 2 the transmittance.

A regression equation including the feature amount obtained as described above as an DMEM and quality as an objective variable is generated in advance. When the quality of a cell mass whose quality is unknown is evaluated, first, the variance of transmittance for each pixel from the transmittance of the cell mass, the degree of change in transmittance, the feature amount based on texture analysis, and the feature amount of light intensity information for each of the divided regions are acquired. Then, the quality of the cell mass can be evaluated by applying these feature amounts to the regression equation. As an example, it is possible to discriminate each of Samples 1 to 6 from the normal cell mass.

Here, when image information is acquired for each of a plurality of wavelengths, a feature amount related to the variation of light intensity information may be obtained based on a combination (for example, a difference, a ratio) of light intensity information between wavelengths.

In the quality evaluation method described above, a feature amount is generated from a variation of a plurality of light intensity information corresponding to each of a plurality of measuring positions in the cell mass. Therefore, the feature amount can reflect the relationship between adjacent cells in the cell mass, the relationship between cells at distant positions, and the like. Since the quality of the cell mass is, for example, an index related to a degree of an ability of cells to aggregate together, when the feature amount reflecting the relationship between cells is used as an index, it is possible to evaluate the quality of the cell mass based on the state of the cell mass on the spot regardless of the cause of cell mass occurrence.

In addition, when the degree of variance of a plurality of light intensity information is generated as one aspect of the feature amount, it is possible to easily derive the variation of light intensity information.

In addition, when the degree of change between the light intensity information at each of the plurality of measuring positions and the light intensity information at the surrounding measuring position is generated as one aspect of the feature amount, the relationship between cells present at positions close to each other in the cell mass is easily reflected in the feature amount.

In addition, when the degree of non-uniformity of the plurality of light intensity information in the cell mass is generated as one aspect of the feature amount, the relationship between cells that are non-uniformly present in the cell mass is easily reflected in the feature amount.

In addition, when the result obtained by comparing at least one from between the variation and basic statistical amounts of the light intensity information for each of two or more regions divided in the cell mass is generated as the feature amount, the state of cells for each region in the cell mass is easily reflected in the feature amount.

While the embodiments of the present disclosure have been described above in detail with reference to the drawings, the specific configuration is not limited to the embodiments. For example, the first to fifth examples are shown as specific examples of the embodiments, but the present invention is not limited thereto. That is, the embodiments of the present disclosure also include embodiments in which the configurations of the first to fifth examples are replaced, and added to each other.

Figure 15:
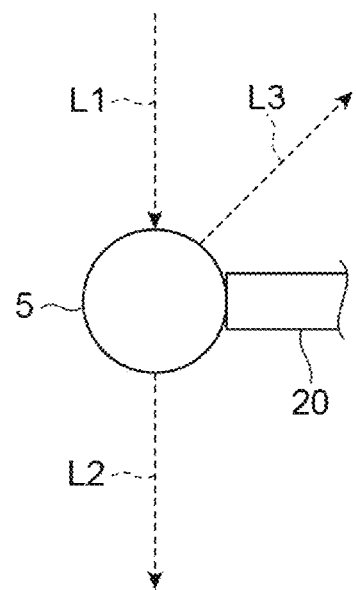
FIG. 15 is a schematic diagram showing another example of a cell mass holding unit in the quality evaluation device.
Figure 16:
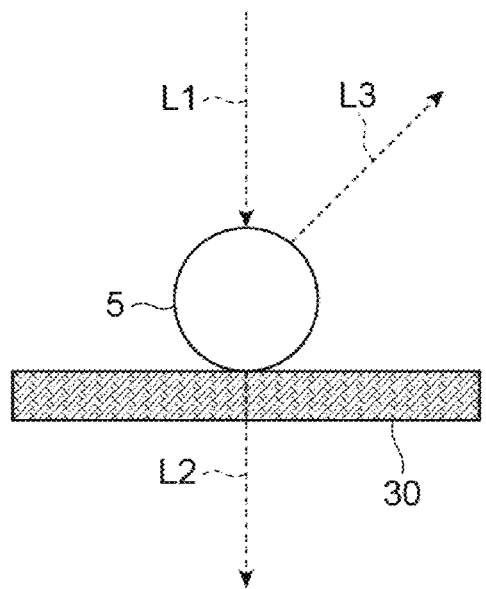
FIG. 16 is a schematic diagram showing another example of a cell mass holding unit in the quality evaluation device.

In addition, an example in which the quality of the cell mass accommodated in the well of the microplate is evaluated is shown, but the cell mass to be evaluated is not limited. FIG. 15 and FIG. 16 are schematic diagrams showing another example of a cell mass holding unit in the quality evaluation device. For example, as shown in FIG. 15, measurement light L1 may be emitted to the cell mass 5 held with a suction tweezers 20. In addition, as shown in FIG. 16, measurement light L1 may be emitted to the cell mass 5 mounted on a sheet component 30 such as a non-woven fabric. In this case, the sheet component 30 may contain a culture solution. In the examples of FIG. 15 and FIG. 16, a 2D sensor may be arranged at a position at which reflected light L3 reflected by the cell mass 5 is input, and reflected light may be input to the 2D sensor. In this manner, the cell mass 5 may be held with any unit as long as measurement light L1 can be emitted and transmitted light L2, reflected light L3 or the like can be received by the 2D sensor, and for example, it may be held in a petri dish.

In addition, in the above embodiment, an example in which cell masses having the same size are evaluated has been shown, but the cell masses to be evaluated are not limited. For example, in a case in which cell masses having different sizes are evaluated, when there is a correlation between the size and the feature amount, the feature amount may be corrected by the size of the cell mass and the number of measurement points. As an example, in the second example, the average degree of change for all pixels in the cell mass may be defined as the degree of change in transmittance of the cell mass.

REFERENCE SIGNS LIST

1 Quality evaluation device
3 Light source
4 Lens
5 Cell mass
7 2D sensor (light receiving unit)
8 Bandpass filter
9 Lens
10 Analysis unit
13 Microplate
15 Well
20 Suction tweezers
30 Sheet component
L1 Measurement light
L2 Transmitted light
L3 Reflected light

What is claimed is:

1. A method for quality evaluation, comprising:
emitting measurement light having a wavelength of 300 nm or more and 2,000 nm or less to a cell mass and acquiring a plurality of light intensity information corresponding to each of a plurality of pixels in the cell mass using a two dimensional (2D) sensor;
generating a feature amount from a variation of the acquired plurality of light intensity information; and
evaluating quality of the cell mass using the generated feature amount as an index,
wherein the generating comprises generating a degree of change between the light intensity information at each of the plurality of pixels and the light intensity information at a plurality of other pixels adjacent to each of the plurality of pixels as one aspect of the feature amount,
wherein the degree of change comprises a sum of absolute values of differences between transmittance in one arbitrary pixel and transmittance in other pixels adjacent to the one arbitrary pixel.

2. The method for quality evaluation according to claim 1, wherein the generating further comprises generating a degree of variance of the plurality of light intensity information as one aspect of the feature amount.

3. The method for quality evaluation according to claim 1, wherein the generating further comprises generating a degree of non-uniformity of the plurality of light intensity information in the cell mass as one aspect of the feature amount.

4. The method for quality evaluation according to claim 1, wherein, in the generating, a result obtained by comparing at least one from between a variation and basic statistical amounts of the light intensity information for each of two or more regions divided in the cell mass is generated as the feature amount.

5. The method of quality evaluation according to claim 1, wherein the feature amount comprises a degree of change in transmittance of the cell mass, wherein the degree of change in transmittance of the cell mass comprises a sum of the degree of change for each of the plurality of pixels.

* * * * *